United States Patent [19]

Williams et al.

[11] 4,332,821

[45] Jun. 1, 1982

[54] 1-ACRYLOYL-3-(SUBSTITUTED)PHENYL UREAS

[75] Inventors: John W. Williams, Vallejo, Calif.; Frank C. Becker, Gurnee, Ill.

[73] Assignee: Abbott Laboratories, North Chicago, Ill.

[21] Appl. No.: 187,242

[22] Filed: Sep. 15, 1980

Related U.S. Application Data

[63] Continuation-in-part of Ser. No. 48,853, Jun. 14, 1979, abandoned, which is a continuation-in-part of Ser. No. 875,253, Feb. 6, 1978, abandoned.

[51] Int. Cl.$^3$ ............................................. A01N 47/28
[52] U.S. Cl. ........................................ 424/322; 564/46
[58] Field of Search ......................................... 424/322

[56] References Cited

U.S. PATENT DOCUMENTS

| | | | |
|---|---|---|---|
| 3,660,484 | 5/1972 | Martin et al. | 424/322 |
| 3,793,213 | 2/1974 | Taber et al. | 252/107 |
| 3,803,227 | 4/1974 | Joos et al. | 260/552 R |

FOREIGN PATENT DOCUMENTS

| | | | |
|---|---|---|---|
| 888316 | 8/1953 | Fed. Rep. of Germany | 260/553 E |
| 43-7138277 | 1/1968 | Japan | 424/322 |
| 46-28116 | 7/1971 | Japan | 424/322 |
| 235012 | 11/1967 | U.S.S.R. | |

*Primary Examiner*—Allen J. Robinson
*Attorney, Agent, or Firm*—Robert L. Niblack; Paul D. Burgauer

[57] ABSTRACT

1-Acryloyl-3-(substituted)phenyl ureas have been found to be highly effective as fungicides when incorporated into or applied to agricultural media, plastics, paints or the like.

5 Claims, No Drawings

1-ACRYLOYL-3-(SUBSTITUTED)PHENYL UREAS

BACKGROUND OF THE INVENTION

This application is a continuation-in-part of our earlier filed application, U.S. Ser. No. 48,853, filed June 14, 1979, which in turn is a continuation-in-part of U.S. Ser. No. 875,253, filed Feb. 6, 1978, both now abandoned.

DETAILED DESCRIPTION OF THE INVENTION

Useful agricultural crops, plant life in general, paints, painted surfaces and plastics often are attacked by various types of common fungi. Particularly, fruit and vegetable bearing plants frequently host fungi which may damage the fruit or vegetable to the point where it cannot be marketed and, therefore, drastic reduction in harvest income can result. Also, plastics and painted surfaces used or stored in moist atmospheres are often attacked by fungi which produces unsightly surfaces.

It has now been found that crops of the above nature, plastics, paints and the like can be protected by applying to such substrates a compound of the formula:

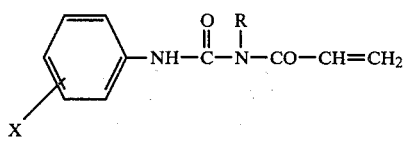

(I)

wherein X represents H, Cl, OR, SR, $NO_2$ or R with each R representing H or a linear or branched saturated loweralkyl group. These acryloyl ureas are effective at concentrations of 10-5000 ppm and these concentrations are not damaging to the plants or crops themselves, and they do not discolor paints to which they are added or plastics in which they are incorporated.

The compounds of the above formula can be applied directly to paints or plastic formulations or they can be applied to agronomical substrates as solutions or dusts. Sprays are preferably prepared from a water-dispersible or from an emulsifyable liquid concentrate. Such concentrates can be made by dissolving the active ingredient in dimethylsulfoxide, tetrahydrofuran, chloroform, tetrahydrofurfuryl alcohol, acetone, a mixture thereof or a mixture of either of these solvents with small amounts of water, lower alkanols, dimethylformamide, dimethylacetamide or the like. Concentrates should contain between 25 and 50% by weight of the acryloyl ureas.

Sprayable dusts can be prepared from the above ureas using customary dusting powders, e.g., finely divided bentonite, chalk, clay, calcium carbonate, silica, kaoline, talc, fuller's earth, etc. and containing agriculturally acceptable wetting agents, detergents, etc. Solid compositions of this nature can also be prepared in the form of wettable powders which easily disperse in water for spraying. Formulations of this type can be prepared in accordance with PESTICIDE FORMULATIONS by Van Valkenberg (Marcel Dekker, Inc., New York 1973) pp 175-186. Solid formulations preferably contain between 25 and 75% by weight of the shown urea.

In order to illustrate the process for using the present invention, reference is made to the following examples which are not to be understood as limiting the invention in any form. The acryloyl ureas are prepared in accordance with known methods such as those described in German Pat. No. 888,316 using acrylamide or N-methylacrylamide as the starting materials.

EXAMPLES 1-3

The antifungal properties of the above compounds were established in accordance with the following examples of standard tests:

(A) *Phytophtora infestans* (Late Tomato Blight). Bonny Test tomato plants, grown to 5-leaf stage in a green-house on Swiss Farm potting soil in 7-ounce styrofoam pots with weekly 20-20-20 fertilizer application at 20°-28° C. day and 15°-20° C. night temperature, are treated with a solution or suspension of the fungicide. Both leaf surfaces are sprayed to run-off with a DeVilbiss atomizer at 10 psi. The formulations are prepared by dissolving the fungicide in an acetone-Tween ® 20 mixture and diluting the solution with water to a fungicide concentration of 1000 ppm.

Two days after the plant treatment, a swarm-spore suspension (10,000/ml) is sprayed on the lower leaf surface with the above atomizer to a point just before run-off. The plants are then maintained at 100% humidity and 17° C. for 24 hours and subsequently kept under the above greenhouse conditions until symptoms appear. The fungicidal activity is judged by the percent of necrosis of the third, fourth and fifth leaves.

(B) *Pyricularia oryze*.

Rice plants are grown to the same stage and under the same conditions as the tomato plants in (A) except that they are thinned to 3 plants per pot. The solution or suspension of (A) is applied in the same fashion.

Two days after the plant preparation, the plants are inoculated as in (A) but with a spore suspension containing 50,000 spores/ml, and maintained as in (A). The fungicidal activity is measured as the index of number of lesions per fourth leaf/leaf area.

(C) *Puccinia recondita f. sp. tritici* (Leaf rust).

The pre-treatment is carried out on Yorkster wheat exactly as in (B) except for using the plants in the 1-leaf stage.

Inoculation follows the above method except that the uredospore suspension contains 20,000 spores/ml. and the plants are maintained as above and judged as in (B) on the basal leaf.

The results, expressed as % of protection are shown below:

| Example | ppm | Test A | Test B | Test C |
| --- | --- | --- | --- | --- |
| X = 3-Cl | 100 | 100 | 99 | 92 |
| R = H | 10 | 32 | 96 | 87 |
|  | 1 | 0 | — | — |
| X = 4-Me | 100 | 100 | 99 | 87 |
| R = H | 10 | 30 | 78 | 71 |
|  | 1 | 0 | — | — |
| X = 4-Cl | 100 | 100 | 99 | 83 |
| R = H | 10 | 85 | 97 | 87 |
| Standard* | 100 | 97 | 100 | 100 |
|  | 10 | 33 | 75 | 67 |
|  | 1 | 4 | 17 | 12 |

*For tests (A) and (C), the test results are compared with industry standard, manganous ethylenebis-(dithiocarbamate known as Maneb ® or Dithane ® M-22. Results of (B) are compared with O-ethyl-S,S-diphenyl phosphorodithioate, known as Hinosan ®, the current standard of the industry. In all tests, the initial 1,000 ppm fungicide solution or suspension is further diluted to determine the activity at 100 and 10 ppm.

As will be noted, the current compounds compare favorably with the results obtained from current industry standards.

EXAMPLE 4

In an in vitro test, some of the compounds of formula I are tested in an agar plate minimum inhibitory concentration (MIC) screen from a solution in dimethylformamide against a challenge mixture of *Rhizoctonia sp* No. 657 and 659. The results show that Compound I where R=H and X represents chlorine or methyl in the 3- or 4-positions or 3,4-dimethyl have an MIC of 10 ppm. Compound I where X is 4-chloro and R is methyl or ethyl also show MIC values of 10 ppm.

EXAMPLE 5

In an in vitro MIC test, the amount of the test compound of Formula I needed to prevent fungi growth is established. In this test, agar containing the test compound at a specified concentration is inoculated with 1 ml. of a broth containing 10,000 units each of *A. niger* and *P. funiculosum*. The agar plates inoculated in this fashion are incubated at 30° C. for 2 weeks and growth of the microorganisms is visually inspected to establish the MIC. The following table shows the results of the ureas of formula I, showing the substituents.

| Compound I | | |
|---|---|---|
| X = | R = | MIC |
| H | H | 100 |
| 2-Cl | H | 100 |
| 3-Cl | H | 10 |
| 4-Cl | H | 10 |
| 2-Me | H | 100 |
| 3-Me | H | 10 |
| 4-Me | H | 100 |
| 2-OEt | H | 1000 |
| 4-OEt | H | 10 |
| 2-OMe | H | 1000 |
| 4-OMe | H | 100 |
| 4-Cl | Me | 10 |
| 4-Cl | Et | 100 |
| 3,4-Me$_2$ | H | 100 |

EXAMPLE 6

In a test similar to that described in Example 5, 1-phenyl-3-acryloyl urea is tested against certain specific fungi. The compound shows an MIC of 10 against *Chaetomium globossum, Myrothecium verrucaria, A. versicolor, Fusarium oxysporium* and an MIC of 100 against *P. citrinum, Alterneria* and *Rhizopus nigricans*.

The corresponding 1-p-tolyl-3-acryloyl urea and the 1-(4-chlorophenyl)-2-acryloyl urea both show an MIC of 10 against *Chaetomium globussum;* the latter compound shows the same activity against *Rhizopus nigricans* while the former shows an MIC of 100 against all the above fungi.

EXAMPLE 7

A cotton fabric sample is soaked in acetone containing 1-phenyl-3-acryloyl urea in such a fashion that after drying, the fabric contains 0.5% by weight of the test compound. The fabric is placed in nutrient agar and incubated for 24 hours at 37° C. After inoculating the agar with mixed spores, *A. niger, A. flavus, C. globusum* and *P. funiculosum* and storing at 28° C. for 14 days, no growth of any of the organisms is observed.

EXAMPLE 8

Wooden tongue depressors are dipped into a modified acrylic paint composition made according to the following method:

| | |
|---|---|
| Water | 215.9 lbs. |
| Anionic surfactant | 10.5 lbs. |
| Non-ionic surfactant | 2.5 lbs. |
| Dispersing agent | 1.5 lbs. |
| Hydroxyethylcellulose | 2.3 lbs. |
| Ethylene glycol | 25.0 lbs. |
| Defoamer | 3.0 lbs. |
| Titanium dioxide | 237.0 lbs. |
| Fungicide of Compound I | 4 lbs./100 gals. |

The above ingredients are dispersed for 20 minutes and then blended with a mixture of:

| | |
|---|---|
| Acrylic emulsion | 390.8 lbs. |
| Long oil alkyd | 30.8 lbs. |
| Cobalt drier | 0.2 lbs. |
| Zirconium drier | 0.6 lbs. |
| Defoamer | 1.0 lbs. |
| Tributylphosphate | 9.2 lbs. |
| Ammonia | 1.0 lbs. |

After the paint is dried, the painted surface is inoculated with a mixture of *A. pullulans, P. funiculosum* and *A. niger*, containing 10,000 spores/ml. of each. The samples are then placed in a mold box for a period of 4 weeks at 30° C. and 90% relative humidity. The following table shows results of the paint samples with the current fungicide, a control (no fungicide) and a sample containing the same amount of Amical 50 (p-tolyl diiodomethylsulfone containing 25% inert materials) and a commercially accepted fungicide. The ratings are: 0 for no growth on sample, 1 for 0-25% growth, 2 for 25-50% growth, 3 for 50-75% growth and 4 for 75-100% growth of spores over the painted surface.

| Compound I (R = H) | Rating |
|---|---|
| X = H | 0 |
| X = 2-Cl | 3 |
| X = 3-Cl | 2 |
| X = 4-Cl | 0 |
| X = 4-Me | 0 |
| Control (no fungicide) | 4 |
| Amical 50 | 0 |

EXAMPLE 9

A further test is carried out on tomato plants grown in accordance with Examples 1-3, Test A, using a suspension of 10,000 spores/ml of *Alternaria solani* (early blight) and the plants are then kept at 21° C. and 100% humidity for 24 hours and maintained and observed as in Test A. With the compound of Formula I (X=4-Me, R=H) at 1000 ppm, a 0.7% necrosis results, while with industry standard Maneb ®, the same concentration results in 1.7%. No injury to the plant is observed in either case.

Although the above examples primarily demonstrate the fungicidal effects of the compounds of Formula I wherein X is loweralkyl, loweralkoxy or chlorine in any of the ring positions of the phenyl moiety, it is noted that when X is nitro or a mercapto group, similar protection of agricultural crops or an industrial substrate is obtained. Particularly, the following compounds produce similar results as shown in Examples 1–3: 1-(4-alkoxy)-3-ethyl-, 1-(4-methylthiophenyl)-, 1-(2- or 4-nitrophenyl)- and 1-(4-propoxyphenyl)-3-acryloyl ureas.

As will be seen from the results of the above accelerated fungicidal tests, fabrics, paints, painted surfaces and crops are well protected by compounds of Formula I against the most common fungi. In many instances, the current compounds are superior in their protective quality to the currently used standards in the respective settings; additionally they are environmentally acceptable.

When crops are to be protected with any of the above compounds, the described wettable powder or emulsifiable concentrate is best applied in an aqueous spray containing 0.0001–0.1% by weight of the fungicide, preferably between 0.001 and 0.05%. These compositions may also contain between 0.1 and 5% by weight of a wetting agent, such as an alkyl sulfate, an alkylaryl sulfonate, a sulfosuccinate, a polyethylene glycol ether, or the like. Dusting powders made with the current fungicides and finely divided, inert diluents preferably also contain the fungicide in the above concentration.

For use in paint or other coatings, the above compounds can be added in amounts of 0.01 to 1.0% by weight, preferably between 0.3 and 0.6%. When used in textiles, including cellulosics, wool, synthetics, a stock solution for treating the fabric is best prepared in such a fashion that when the continuously moving woven or nonwoven fabric travels through the bath containing the above compound, it picks up between 0.05 and 1.0% by weight of said compound, calculated on a dried weight. The necessary level of fungicide can thus be added to any of the various solutions that are ordinarily used in the finishing treatment of textiles.

For use as a fungicide in a polymeric material suitable for extruding, molding or foaming, the compound of Formula I is best added to the polymeric powder or to one of the monomer mixes from which the polymer is formed. In these instances, the fungicide is preferably used in such a concentration that the final structure contains between 0.1 and 1.0% by weight thereof.

We claim:

1. The process of protecting substrates susceptible to attack by fungi against attack by common fungi consisting essentially in applying to such substrates an antifungally effective amount of a compound of the formula

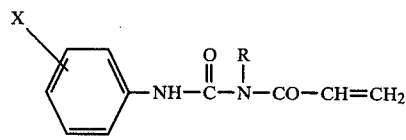

wherein X is Or, SR or R with R being H or loweralkyl.

2. The process of claim 1 wherein said amount is between 10 and 5000 ppm.

3. The process of claim 1 wherein X is methyl.

4. The process of claim 3 wherein said methyl is in the m-position and R is H.

5. The process of claim 3 wherein said methyl is in the p-position and R is H.

* * * * *